United States Patent [19]

Foley

[11] 4,250,165
[45] Feb. 10, 1981

[54] METHOD OF STABILIZING FRAGRANCE OILS

[75] Inventor: Lary L. Foley, San Francisco, Calif.

[73] Assignee: The Clorox Company, Oakland, Calif.

[21] Appl. No.: 962,487

[22] Filed: Nov. 20, 1978

Related U.S. Application Data

[63] Continuation of Ser. No. 782,565, Mar. 29, 1977, abandoned.

[51] Int. Cl.³ .................. A61K 7/46; A61L 13/00
[52] U.S. Cl. ........................ 424/76; 252/522 R; 424/16; 424/19
[58] Field of Search .............. 424/76, 358; 252/522; 239/44

[56] References Cited

U.S. PATENT DOCUMENTS

| | | | |
|---|---|---|---|
| 2,691,615 | 10/1954 | Turner et al. | 239/54 |
| 2,773,774 | 1/1957 | Buslik | 426/387 |
| 3,215,719 | 11/1965 | Allen et al. | 260/448.8 |
| 3,216,882 | 11/1965 | Feldt et al. | 161/109 |
| 3,261,746 | 7/1966 | Copley | 424/35 |
| 3,423,022 | 1/1969 | Varley | 239/53 |
| 3,424,849 | 1/1969 | Conklin et al. | 424/365 |
| 3,567,118 | 3/1971 | Shepherd et al. | 424/81 X |
| 3,685,734 | 8/1972 | Pacioreh et al. | 424/22 X |
| 3,767,787 | 10/1973 | Segal | 424/76 |

FOREIGN PATENT DOCUMENTS

1502852  3/1978  United Kingdom .

OTHER PUBLICATIONS

American Perfumery and Cosmetology, vol. 77, No. 10, pp. 17–18, (1962).
American Perfumery and Cosmetics, vol. 77, No. 10, (1962), pp. 132–133.

*Primary Examiner*—Allen J. Robinson
*Attorney, Agent, or Firm*—Phillips, Moore, Weissenberger, Lempio & Majestic

[57] ABSTRACT

Compositions of fragrance oils are stabilized with respect to potency and aesthetic quality toward the effects of heat and age by including in the formulations a quantity of alkylphenol ethers of polyethylene glycol, or more specifically, alkyl phenoxy polyethoxy ethanols wherein the polyether chain averages from 5 to 13 moles of ethylene oxide, and the alkyl portion of the molecule ranges from 6 to 20 carbon atoms. The alkyl portion of the molecule may be branched, unbranched, saturated or unsaturated. The oils are stabilized in respect to durability or intensity of odor with time and are rendered relatively insensitive to the deleterious effects of heating and/or aging in the presence of air. The presence of the stabilizers also eliminates the phenomenon of the "migration" of the perfume oil caused by repeated vaporization and condensation within an enclosed space. In addition, the inclusion of the stated stabilizers, when judiciously used, tends to "round out" or "smooth out" the overall perception of the odor characteristics of the particular oils utilized, often increasing the aesthetic value of the fragrance composition when so used.

10 Claims, 4 Drawing Figures

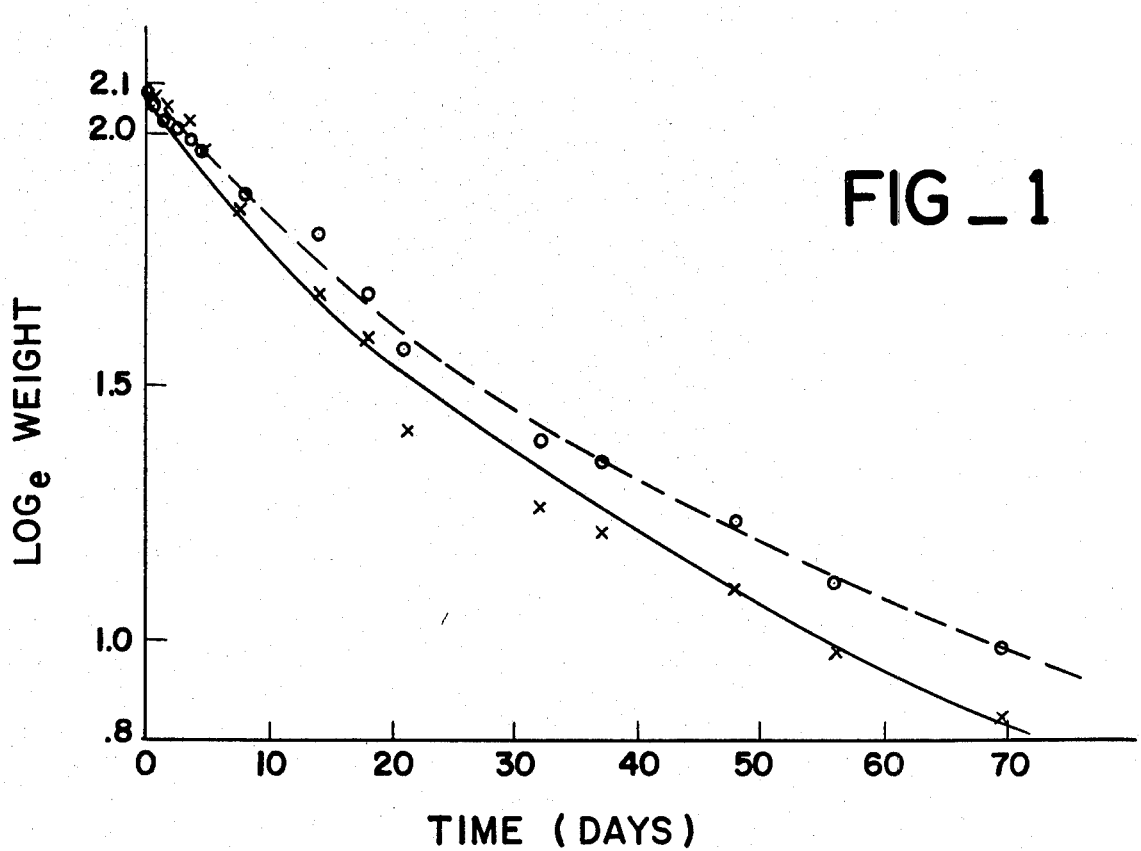
FIG_1
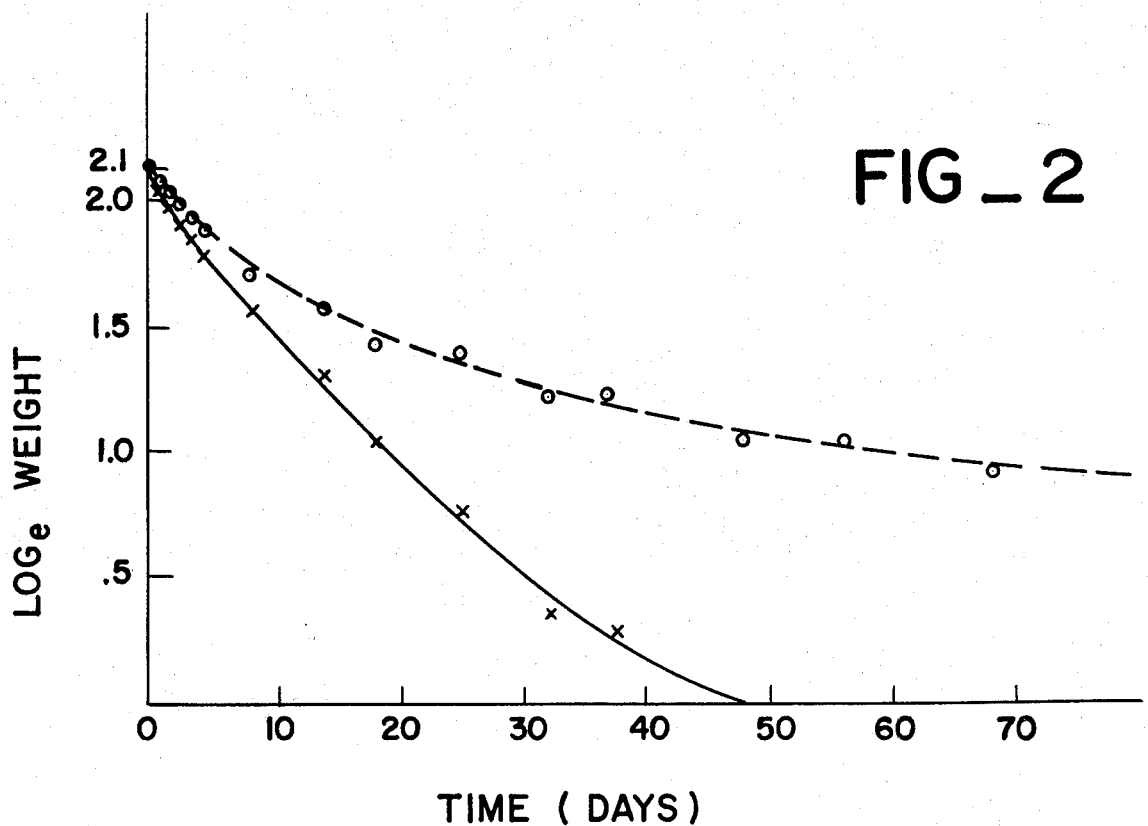
FIG_2

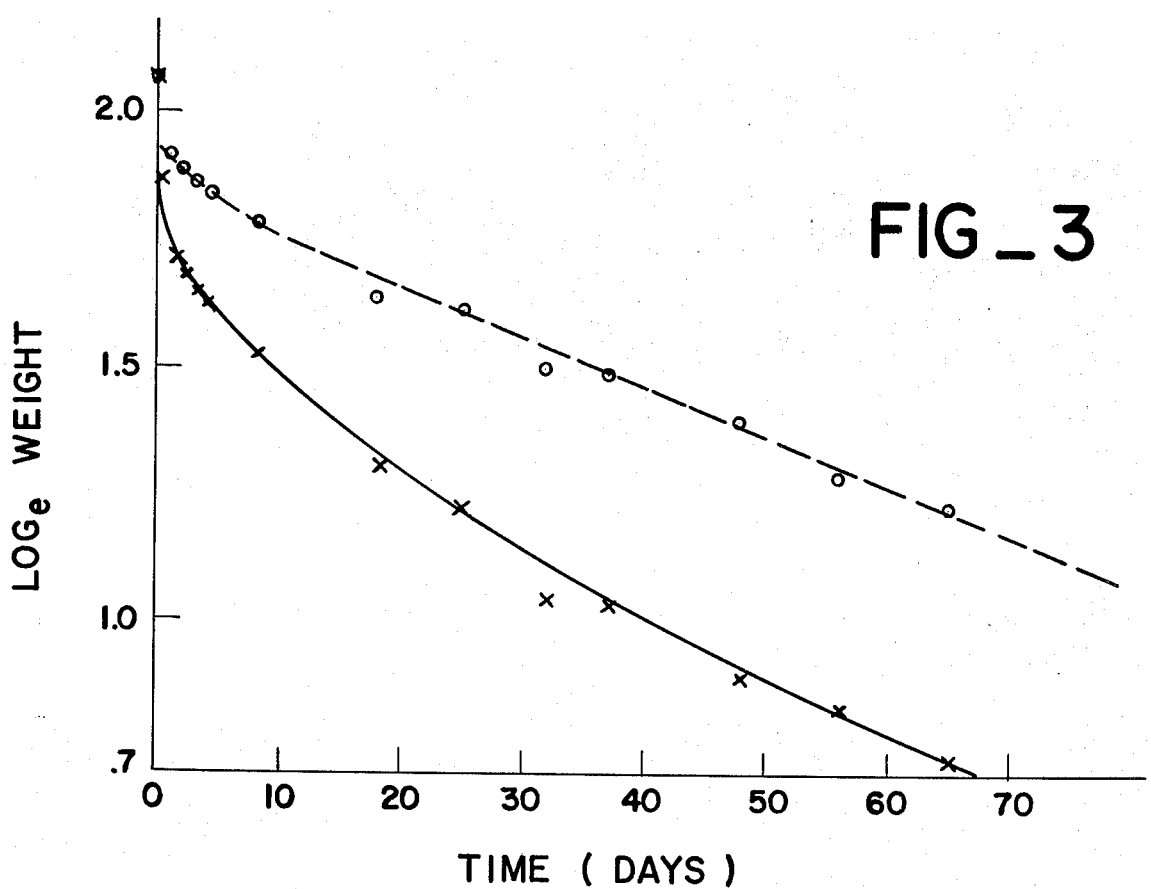
FIG_3
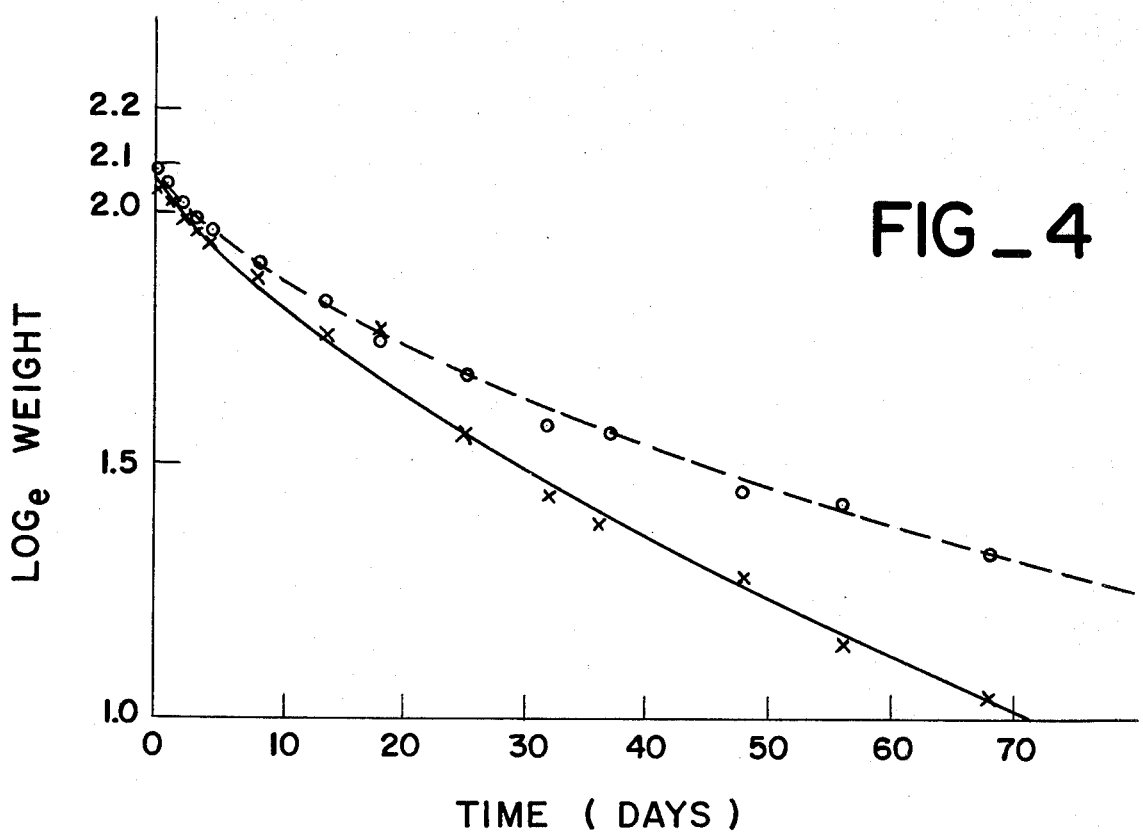
FIG_4

METHOD OF STABILIZING FRAGRANCE OILS

This is a continuation of Ser. No. 782,565, filed Mar. 29, 1977 now abandoned.

BACKGROUND OF THE INVENTION

Air fresheners or space deodorants have come into increasing use in the household market in recent years. Their sales and use have increased rapidly and represent a substantial market. Such products usually consist of liquid, aerosol, or more generally, a semi-solid composition comprising various oils and other components packaged in a container provided with openings to expose the fragrance composition to the atmosphere. The fragrance components volatilize into the atmosphere to mask or otherwise decrease the perception of malodor that may be present therein.

Almost invariably the freshener compositions are comprised of volatile materials that lend a distinct fragrance of their own to the atmospheric environment. While the fragrances preferred by consumers change from time to time they usually fall into categories such as those of "floral scents", "citrus scents", "pine scents", and "herbal scents" and other less distinct groupings referred to as "fantasies". All such scents impart their own distinct fragrance to the atmosphere and all rely upon a number of theoretical mutually operative mechanisms to lower the perceived strength of malodor.

Since all such fragrances rely upon these effects, they are only effective to the extent that they volatilize efficiently to impart a significant amount of active material to the atmosphere to combat malodors present in their vicinity. While such compositions at the present state of the art, are quite effective in producing a high or adequate level of active volatile material in the atmosphere when new and fresh, they usually rapidly lose their potency, or are so volatile that the active materials are completely evaporated within a short period of time, say within a few days when continuously exposed to the ambient atmosphere.

It is therefore of interest to produce compositions that retain their effectiveness over longer periods of time whereby space deodorants may have an extended effective life and the resultant economic benefit will be realized by the consumer.

In the past, efforts to solve this problem have resorted to compositions utilizing less volatile fragrances, or formulations wherein the fragrances tend to be relatively "immobilized". In the first instance, the less volatile fragrances may be so non-volatile as to fail to produce an effective level of fragrance or active material in the ambient atmosphere. In the second instance, resort is often made to solid or semi-solid gels or similar formulations which reduce the volatility of the active components by requiring that they migrate through the mass of the gel or semi-solid toward its atmospheric interface prior to volatilization, thereby increasing the active life of the composition. Such solid or semi-solid compositions, however, are tedious to formulate; requiring mixing, heating, pouring into molds, or otherwise forming the gels and semi-solids, so that the active components are effectively volatile without being too tightly bound within the formulation such that their activity is unduly depressed. In the case of aqueous alginate and carrageenan based gels, the unsightly shrinkage over a period of time of the semi-solids thus produced is, in practice, impossible to avoid.

It will become obvious to one skilled in the art that the above disadvantages are avoided by use of the present invention.

BRIEF DESCRIPTION OF THE INVENTION

The present invention relates to air freshener formulations and more specifically to air freshener formulations wherein the following benefits beyond those of the current state of the art are realized.

1. Reduction of the rate of volatilization of the active components of the odor counteractant composition.
2. Prevention of migration of the perfume oil, caused by repeated vaporization and condensation in an enclosed space to surfaces other than those to which the oil was applied.
3. Stabilization of the aesthetic qualities of the fragrance of the active composition by the reduction of the rate of its degradation due to heating, aging and intrinsic or extrinsic chemical reaction or instability.
4. Stabilization of the aesthetic quality by "rounding" or "smoothing" of performe oils, when said stabilizers are judiciously applied by one skilled in the perfumery art.

The above listed benefits are achieved by incorporating a quantity of an alkylphenol ether of polyethylene glycol into the formulation. In particular, alkyl phenoxy polyethoxy ethanols averaging from 9 to 12 moles ethylene oxide, and alkyl radicals ranging from 3 to 9 carbon atoms therein are especially effective in achieving the above enumerated benefits.

The addition of such alkyl phenoxy polyethoxy ethanols to "air freshener" quality formulations also appears to improve the olfactory quality of the formulation and to "round out" or to "smooth" the fragrance to make it more pleasing to the person receiving the fragrance, providing the fragrance composition is judiciously chosen, preferably by one skilled in the art of perfumery. In some instances the result of the addition of said "ethoxylates" can result in an effect which might be termed "dulling" or as supression of "topnote" resulting in a "flatting" effect. Judgement must be exercised in such a case, whether the benefits of 1, 2, and 3, above, outweight the possible undesirable effect in 4 above. The case more often, however, is one of enhancing the aesthetic value of "air freshener" quality oil; making it perceived as less "harsh" or less "chemical" smelling.

The addition of alkyl phenoxy polyethoxy ethanols to the formulation also reduces the undesirable characteristics of fragrance oil formulations to evaporate and recondense in a closed space such as a package to form beads or droplets of pure fragrance oil. The "evaporation-condensation" phenomenon in the past has hindered the marketing of such formulations in other than semi-solid form or in pressurized containers and has prevented their being effectively marketed by the simple absorption of said fragrance oils onto any number of inexpensive absorbent substrates such as paper pads, etc. Addition of the alkyl phenoxy polyethoxy ethanols reduces this undesirable characteristic to the extent that the liquid formulations may be absorbed on any suitable porous material and be packaged in a closed container without the evaporation and recondensation of the fragrance oil to adjacent inner surfaces of the package.

It is therefore an object of this invention to prepare air freshener formulations having a longer effective life.

It is another object of the invention to extend the useful life of fragrance oils.

It is another object of the invention to stabilize fragrance oils against the effect of degradation due to heating, aging, intrinsic or extrinsic chemical instability.

It is still another object of the invention to provide air freshener formulations that do not migrate in the container thereof but tend to remain in the substrate into which they were absorbed.

Other benefits and advantages of the invention will become apparent from a review of the following specification and claims as well as the drawings wherein:

FIGS. 1, 2, 3 and 4 are all representations of the loss in weight with time of four different fragrance oil formulations, as compared with the same fragrance formulations compounded with an added quantity of alkyl phenoxy polyethoxy ethanols.

DETAILED DESCRIPTION OF THE INVENTION

Air freshener formulations generally comprise as an essential component, one or more fragrance oils; or in lieu of these, what could be considered as being more commonly practiced in the present state of the art of "air freshener" fragrance technology, man-made "synthetic" mixtures. These "synthetics" approximate essential oils in their olfactory impression and often consist of essential oil fractions, and chemical odorants of which there is no counterpart found in nature, and chemical odorants known to have odor counteractant activity. The substances function in an air freshener device by an evaporative action to distribute their fragrance and active materials into the surrounding air spaces. These essential oils are standard articles of commerce and are derived from a great number of plant and animal sources, and virtually all have their "synthetic" counterparts as a result of advances in synthetic organic chemistry. Generally, many fragrance oils or "synthetics" are compounded together to produce the fragrance effects desired by the compounder.

The fragrance oils and synthetics, in turn, are compounded with additional components that serve several functions; often the fragrance oils and "synthetics" themselves serve in these functions. Among these functions are so called "fixation" of the fragrance to increase its permanence, solubilization of the oils, and volatilization control agents, etc. In addition, in many instances, these components, are combined with other materials such as alginates and carrageenans in an aqueous medium to produce a semi-solid gel in the event that the fragrances are to be packaged as non-liquid formulations.

It has now been determined that the addition of a quantity of alkyl phenoxy polyethoxy ethanol, to the fragrance oil formulation, results in a stabilization of the fragrance oils whereby the effective "life" therefore is considerably extended. In this context, "life" is taken to mean the extension of the fragrance oils ability to produce effective levels of fragrance in the surrounding environment over a period of time greater than is the case in the absence of these ethoxylates.

The presence of these materials results moreover in additional advantages. Specifically, the recondensation of the fragrance oils on nearby surfaces, i.e., the package, is essentially eliminated whereby the formulation may be prepared in a liquid form and absorbed on any porous material, such as blotting paper and the like thereby to produce a "dry" product. This effect could be thought of as a corollary to the extension of the life of the composition due to its depression of overall vapor pressure and the high affinity that alkyl phenoxy polyethoxy ethanols have for organic vapors in general. Either or both of these effects are operative to prevent migration of the fragrance oil from the absorbent substrate to other areas where condensation of the oil is undesirable.

In the preferred formulations of the invention, fragrance oils, man-made "synthetic" mixtures, essential oil "fractions" and "chemical odorants", and chemical odorants known to have counteractant activity generally received, in practice as, a "finished" composition are combined with alkyl phenoxy polyethoxy ethanols to produce the desired air freshener product. These materials may be in any standard formulation or variation thereof; the formulation, in this respect, is prepared to produce the desired fragrance or odor counteractant activity in accordance with state of the art of perfumery technology.

Any number of fragrances are useful in the air freshener formulation. Some examples are: Citronellol, hydroxy-citronellol, rhodinl, eugenol, genanoil, rose oil, heliptropine, peru balsam, ylang-ylang oil, isoeugenol, bergamot, coumarin, musk, and all or any of the "synthetic" counterparts of the foregoing, and odorant chemicals of which there is no counterpart in nature. These materials are generally used in combination to achieve the desired fragrance and odor counteractant effect.

Components to enhance or vary fragrances are multitudinous and are comprised of virtually all organic functional groups including alcohols, esters, ketones, aldehydes, acids, terpines, ethers and other materials of a highly complex nature, to name a few. Some of the foregoing materials function not only as odorants but to dual purposes such as solvents, viscosity controlling agents, etc.; while others used in trace amounts may serve as fragrance modifiers. All of the above may be included in the present state of the art of perfumery in the formulation of an odor counteractant compound in accordance with the desires of the formulator.

To this prepared, sometimes very complex composition of fragrances, enhancers and modifiers is added from about 5% to 95% by weight of alkylphenol ethers of polyethylene glycol stabilizer. In the preferred formulations the compounds of the class octylphenyl ethers of polyethylene glycol are used. Such compounds have the general formula:

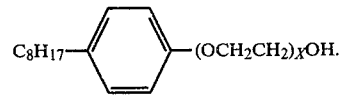

Those agents of the above structure wherin X is from 9 to 12 are especially preferred in the formulation.

The octylphenol ethers of polyethylene glycols are commercially available (Rohm and Haas, under the name *Tritons*) as a mixture of polyoxy ethylene chains of lengths of 1 to 30 oxyethylene units. These are generally secured as mixtures of varying polyoxyethylene chain lengths distributed according to the Poisson distribution, and in practice, chain length can be reasonably well specified and are articles of commerce. Those agents having an average chain length from 9 to 12 moles of ethyleneoxide are especially preferred in the formulations of the invention.

The alkylphenol ethers of polyethylene glycol are often used, due to their surface-active properties, to render perfume oils soluble in, dispersed in, or otherwise integrated into aqueous media.

Most generally, the "stabilized" fragrance formulation is, in the context of this invention, absorbed in a porous matrix, that is generally a type of blotting paper which is then packaged in a sealed container for storage and subsequent distribution for retail sales. In use, the container is unsealed and opened to release the fragrance into the surrounding environment.

It has been found that the addition of alkyl phenoxy polyethoxy ethanol stabilizes the fragrance components so as to appreciably extend their useful life, i.e., prolong the time during which the formulation retains its ability to effectively provide the desired level of fragrance in its surrounding while being continuously or continually exposed to the ambient atmosphere; protect the aesthetic qualities of the fragrance of the active compound by reduction of the rate of its degradation due to heating and aging, and intrinsic and extrinsic chemical reaction or instability; prevention of migration of the perfume oil caused by repeated vaporization and condensation to surfaces other than those to which the oil was applied; and improvement of the aesthetic quality or "smoothing" of the perfume oil when said invention is judiciously applied by one skilled in the perfumery art.

One method of determining the "life" of the fragrance oil formulation absorbed as described in the foregoing, is to measure its weight as a function of time. Such loss is due to evaporation of the various components to the surrounding atmosphere. In order to test the effectiveness of the formulations of the invention, four fragrance oil test compounds were prepared. Eight grams of each test fragrance oil formulation were absorbed into a 4 millimeter thick blotter paper which had a total of 80 sq. inches evaporative surface area. Second, eight gram samples each of the same 4 fragrance oil formulations were then mixed with 8 grams of octylphenol polyethoxy ethanol (average 9–10 ethylene oxide groups) and the individual samples were absorbed on said blotter paper which was identical in size with those previously noted. All blotter paper samples were then allowed to evaporate at controlled and identical conditions into the surrounding atmosphere and were reweighed periodically. The four test compositions of the fragrance oil formulations were as follows:

| Parts by Weight | Formula I |
|---|---|
| 225 | Amylcinhamic Aldehyde |
| 670 | Benzyl Benzoate |
| 3400 | Citronellol |
| 450 | Diethylphthalate |
| 1460 | Hydroxycitronellol |
| 225 | Indole 10% in Diethylphthalate |
| 2420 | Phenylethyl Alcohol |
| 1150 | Rhodinol |
| 10000 | |

| | Formula II |
|---|---|
| 275 | Aaldehyde C-8 10% in Diethylphthalate |
| 1850 | Eugenol |
| 600 | Geraniol |
| 470 | Indole 10% in Diethylphthalate |
| 730 | Linalyl Acetate |
| 2500 | Methyl Anthranilate |
| 3150 | Petitgrain Oil |
| 425 | Phenylethyl Alcohol |
| 10000 | |

| | Formula III |
|---|---|
| 324 | Acropal (Firmenich) |
| 39 | Bois De Rose Oil, Brazil |
| 26 | Heliotropine |
| 114 | Tincture Civet 3% in Alcohol 39-C |
| 229 | Iralia, Pure (Firmenich) |
| 110 | Peru Balsam, Decolorized, 10% in Alcohol 39-C |
| 129 | Violette AC (Ichine Alpha) |
| 14 | Ylang Oil II |
| 15 | Irophore (Firmenich) |
| 10000 | |

| | Formula IV |
|---|---|
| 225 | Amyl Salicylate |
| 91 | Benzyl Salicylate |
| 192 | Coumarin |
| 248 | Isobutyl Salicylate |
| 28 | Isoeugenol, Extra |
| 25 | Musk Ambrette |
| 28 | Violette AC (Ionone Alpha) |
| 28 | Ylang Oil II |
| 135 | Bergamot 136 (Synthetic) |
| 10000 | |

FIGS. 1, 2, 3 and 4 of the drawing present, respectively, plots of the natural logarithins (loge) of the sample weights as against time (days), for each of the sample formulations 1, 2, 3 and 4. In each figure the curves indicated by the 0's present data for the fragrance oil-octylphenoxy polyethoxy ethanol formulations; while the curves indicated by the X's present data for the fragrance oil formulations alone.

A review of each of the FIGS. will clearly indicate that the invention formulations suffered considerably less weight loss over time as compared to the fragrance oil formulations alone.

In a second experiment to detect "migration", the blotters were placed in "cage-like" containers open to the ambient air. These containers had a covering "jacket" which could be completely or partially removed to permit access to the ambient air. But in this experiment the jackets were sealed and then subjected to temperature fluctuations which might be typical of those encountered in the course of distribution and sale of such a device. The temperature variations were on the order of 50° (50° F.–100° F.). Many experiments of this nature were carried out not only with the above test compounds but with a large number of typical "air freshener" compounds. At the end of varying amounts of time (from 1 week to 9 months) the containers were opened and checked for migration or recondensation of the formulation on the inner surfaces of the container. No such migration or recondensation was noted in the case of those compositions which contained octylphenoxy polyethoxy ethanol. Thus, it appears that the addition of this material and its analogs to fragrance oil formulations modifies their vaporization-condensation properties by either lowering the total vapor pressure of the fragrance oil mixture and/or by modifying their recondensation behavior. This may be explained by the stabilizer's high affinity for organic vapors, which prevents the recondensation of the fragrance oil on surrounding container surfaces.

In addition, the above test formulations and a large number of typical "air freshener" formulations were sealed in the above described devices and were subjected to temperatures which normally destroy much of the aesthetic quality of such fragrance oils. It was found with the above test mixtures and most commercial "air freshener" fragrance compounds that one week of a temperature of 140° F. was sufficient, by sensory panel evaluation, to seriously impair the olfactory quality of the oils. On the other hand, when the same oils and test compounds were mixed in a ratio of 1:1 with octylphenol polyethoxy ethanol, there was generally reported by test panel members a dramatic reduction in the amount of degradation due to the heat encountered by the oils. The upper temperature limit in normal shipping practices of commercial articles is commonly considered to be 140° F.; but even brief periods at this temperature in devices such as these in which there is a high ratio of air to oil would result in the degradation of the perfume oil and an attendant decrease in overall aesthetic value.

Similar experiments as the above were carried out at a constant temperature (100° F.) with aging as a single variable. Over a period of nine months to a year at 100° F. olfactory panels found distinct, and in some cases dramatic, differences between fragrance compositions "protected" by the ethoxylates of this invention compared to those to which no such protection was afforded. These effects have been observed in a very large number of "air freshener" compounds and in great detail in the test compounds named above. The above test compounds were found to be easily degraded by heating and aging in the absence of ethoxylates additives.

The mechanisms as to why ethoxylates of this series can produce what is essentially a chemical stabilization of the aesthetic qualities of the fragrance of the compositions through the reduction of the rate of degradation by heating and aging, and intrinsic chemical instability may be explained by the following hypothesis. The individual ingredients which comprised the fragrance formulation are sequestered by the alkyl phenoxy ethanol chain so as to separate the ingredients one from another, to thus prevent the interaction one with another, and to so bind them along the ethoxylate molecule such that they are resistant to the oxidative effects of the atmosphere contained within the device. This apparent "chemical" stabilizing of what appears to be fragrance oils in general was a completely unexpected and even startling outgrowth of experiments designed to prolong the effective life of air freshener devices.

What is claimed is:

1. A stabilized fragrance formulation consisting essentially of fragrance oils in combination with with an alkylphenoxy polyethoxy alcohol present in an amount of from about 5 to 95% by weight of the total formulation, and wherein there are from 9 to 12 ethylene oxide moieties on the average in the polyethoxy chain which forms the polyethoxy portion of the alkyl phenoxy polyethoxy alcohol.

2. The formulation of claim 2 wherein the alkylphenoxy polyethoxy alcohol is the octyl phenoxy compound.

3. A method for counteracting the vaporization and redeposition of perfume oils on the surfaces of containers in which said perfume oils are stored and dispensed consisting of admixing into said perfume oils from 5 to 95% by weight of an alkylphenoxy polyethoxy alcohol, and wherein there are on the average from 9 to 12 ethylene oxide moieties in the polyethoxy chain which forms the polyethoxy portion of the alkyl phenoxy polyethoxy alcohol.

4. The method of claim 3 wherein said alkyl henoxy polyethoxy alcohol is an octyphenoxy polyethoxy ethanol.

5. The method of claim 3 wherein said alkylphenoxy polyethoxy alcohol is a nonylphenoxy polyethoxy alcohol.

6. A method for essentially eliminating the recondensation migration of fragrance oils on the surfaces of a container in which said fragrance oils are stored and dispensed, consisting of admixing with the fragrance oils from about 5 to 95% by weight of an alkylphenoxy polyethoxy ethanol, wherein there are on the average from about 9 to 12 ethylene oxide moieties in the polyethoxy chain which forms the polyethoxy portion of the alkylphenoxy polyethoxy ethanol, thereafter absorbing said admixed fragrance oils and alkylphenoxy polyethoxy ethanol on a porous absorbant matrix, and placing said matrix and absorbed admixture within said container.

7. The method of claim 6 wherein the matrix is a spongy material.

8. The method of claim 6 wherein the matrix is blotting paper.

9. A method for stabilizing the volatilization and odor of a fragrance oil consisting of preparing a formulation consisting essentially of two components by admixing said fragrance oil as a first component with from about 5 to 95% by weight of the total formulation of an alkyl phenoxy polyethoxy alcohol wherein there are from about 9 to 12 ethylene oxide moieties on the average in the polyethoxy chain which forms the polyethoxy portion of the alky phenoxy polyethoxy alcohol, as a second component of the formulation.

10. The method of claim 9 wherein the alkyl phenoxy polyethoxy alcohol is selected from the octyl phenoxy polyethoxy alcohol or the nonyl phenoxy polyethoxy alcohol.

* * * * *